(12) United States Patent
Sorribes

(10) Patent No.: US 7,850,702 B2
(45) Date of Patent: Dec. 14, 2010

(54) CLAMP FOR CORRECTING THE EXTERNAL EAR AND METHOD OF USING THE CLAMP

(76) Inventor: Michael Miravet Sorribes, Jyllingehøj 3, Jyllinge (DK) 4040

(*) Notice: Subject to any disclaimer, the term of this patent is extended or adjusted under 35 U.S.C. 154(b) by 348 days.

(21) Appl. No.: 11/378,680

(22) Filed: Mar. 17, 2006

(65) Prior Publication Data

US 2006/0184184 A1 Aug. 17, 2006

Related U.S. Application Data

(63) Continuation of application No. PCT/DK2004/000620, filed on Sep. 17, 2004.

(30) Foreign Application Priority Data

Sep. 18, 2003 (DK) .............................. 2003 01359

(51) Int. Cl.
*A61B 17/08* (2006.01)
(52) U.S. Cl. ........................................ 606/151
(58) Field of Classification Search .......... 606/151, 606/157, 201, 204.25, 204.35, 204.45, 207, 606/1; 24/521, 517, 518
See application file for complete search history.

(56) References Cited

U.S. PATENT DOCUMENTS

| | | | | |
|---|---|---|---|---|
| 3,608,565 A | * | 9/1971 | Ensign | 132/212 |
| 4,187,838 A | | 2/1980 | Dubrowski | 128/76 |
| 5,282,812 A | * | 2/1994 | Suarez, Jr. | 606/158 |
| 5,444,994 A | * | 8/1995 | Poorting et al. | 63/14.3 |
| 5,662,679 A | * | 9/1997 | Voss et al. | 606/204 |
| 5,899,918 A | * | 5/1999 | Knott et al. | 606/204 |
| 6,517,557 B1 | * | 2/2003 | Sorribes | 606/151 |
| 2002/0062110 A1 | | 5/2002 | Sorribes | 604/304 |

FOREIGN PATENT DOCUMENTS

| | | |
|---|---|---|
| DE | 140440 | 8/1902 |
| WO | WO 94/09731 | 5/1994 |
| WO | WO 00/09050 | 2/2000 |
| WO | WO 01/06967 A1 | 2/2001 |

* cited by examiner

*Primary Examiner*—Kevin T Truong
(74) *Attorney, Agent, or Firm*—Winston & Strawn LLP

(57) ABSTRACT

A clamp in form of a mainly U-shaped or V-shaped device serves for non-invasively affecting a cartilage fold on for example the exterior ear by a stretching and compressive force. The clamp is shaped as a V, in which the angle α between the legs of the V prior to use is equal to or smaller than 90°, and the angle β between the legs of the V, in use mounted on a cartilage fold, is smaller than the angle α. The clamp is made of a material that can be given a permanent deformation and which therefore is able to maintain a constant pressure on local, opposite areas of the cartilage fold.

17 Claims, 4 Drawing Sheets

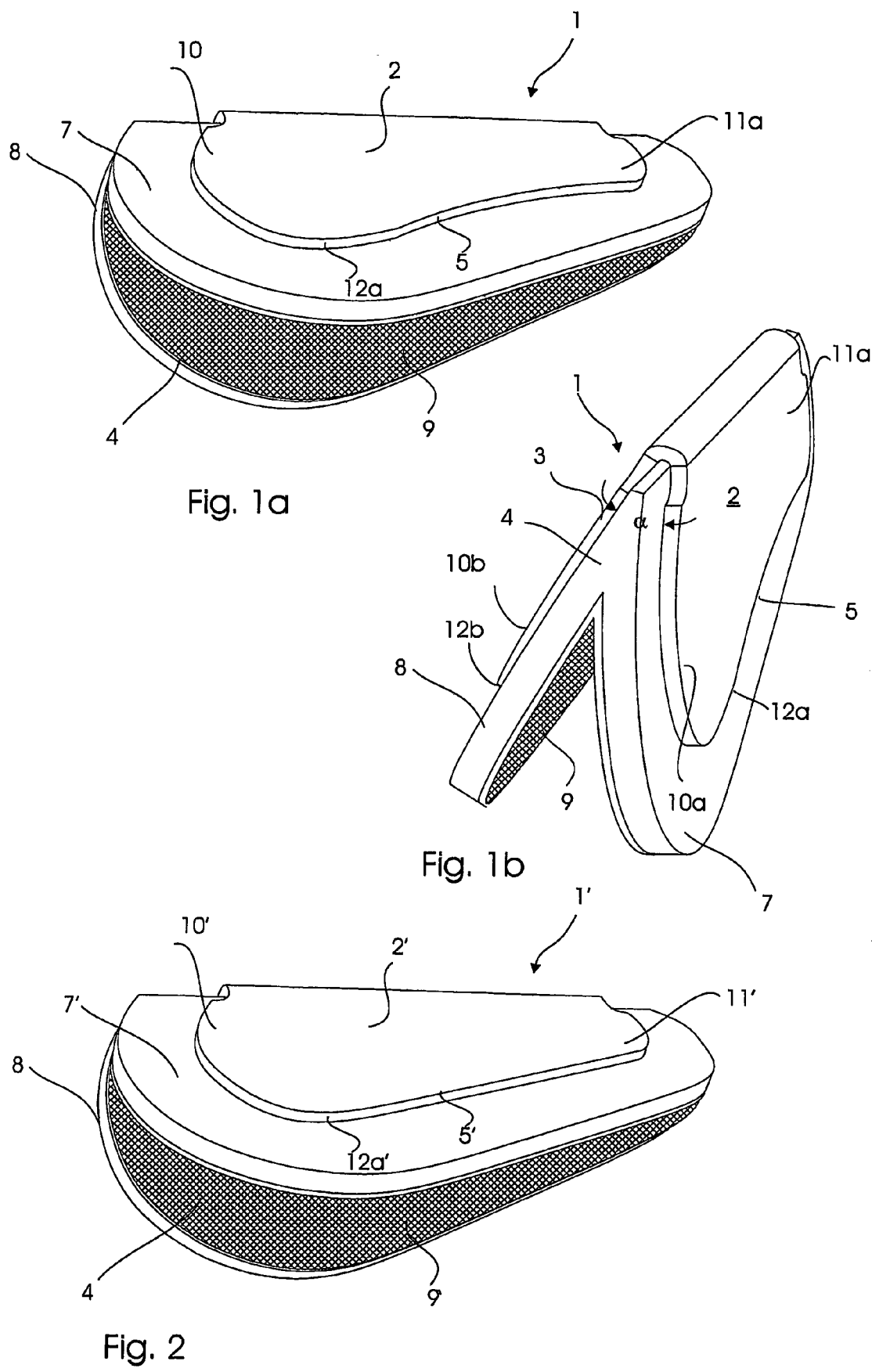

CLAMP FOR CORRECTING THE EXTERNAL EAR AND METHOD OF USING THE CLAMP

CROSS-REFERENCE TO RELATED APPLICATIONS

This application is a continuation of International application PCT/DK2004/000620 filed Sep. 17, 2004, the entire content of which is expressly incorporated herein by reference thereto.

BACKGROUND ART

The invention relates to a clamp in form of a mainly U-shaped or V-shaped device for non-invasively affecting a cartilage fold on e.g. the exterior ear with stretching and compressive forces.

Kids with jug-ears, i.e. lacking or having weakly developed anthelix and crura of anthelix, are often teased but also grown ups with untreated jug-ears can experience these as a physical handicap.

Surgical procedures for treating jug-ears and similar ear disorders will be known to a person skilled in the art and will not be discussed any further here. However, invasive correction is painful and requires local or general anaesthesia just as it leaves cosmetically disfiguring scars.

From the inventor's own International Patent Application No. WO 00/09050 is known an innovative device. This known device has a female mould and male mould connected by a pivoting connection and able to permanently deform the cartilage in a selected zone of the ear from opposite sides.

This treatment has proven effective to especially smaller children whose cartilage is still relatively soft and therefore easily can be modulated. Today, a large number of patients all over the world are successfully treated.

Treatment by means of this known device can advantageously be replaced or supplemented by means of the double coated fixture known from the inventor's own International Patent Application No. WO 01/06967. The fixture is adhered on the back of a jug-ear so that it covers most of the area of the ear lacking anthelix and where a permanent cartilage deformation already has been initiated or is wanted. Subsequently the artificial anthelix is folded by the two parts of the plaster being adhesively contacted to each other. Anthelix is gently kept stuck together from the back of the ear while the cartilage is allowed to heal in the damaged state. However, it has turned out that some patients who receive non-invasive treatment for jug-ears by means of the above devices have to be treated for a very long time.

This is due to the elasticity of the cartilage of the exterior ear. This elasticity means that the ear has a tendency to return to its original shape when the ear e.g. has been bent or deformed. This tendency has for some of the patients been so marked that treatment by means of the above device, in which the pivoting connection between female mould and male mould is a U-shaped spring, has proven insufficient as the spring power has not been able to provide the necessary deformation of the cartilage.

SUMMARY OF THE INVENTION

A significant aspect according to the present invention is to provide a device of the kind mentioned in the opening paragraph, by means of which the shape of an exterior ear can be corrected quicker and more effectively than hitherto known.

The novel and unique feature according to the invention, whereby this is achieved, is the fact that the clamp is shaped as a U or V and is made of a material such as a deformable metal that can be given a permanent deformation.

A clamp or cramp having such a form can keep the ear in an excessively deformed state, in which the clamping force is only exerted on a small selected local area of the artificially constructed cartilage fold, but on the other hand vertex of the ear fold is stretched and pulled until the elastic cartilage fibers have been gently stretched and given a permanent lesion. The lesion will initiate healing of new cartilaginous scar tissue and that this tissue fills the created lesion cavities as newly formed cartilaginous tissue advantageously will be formed in form of the cartilage structure of a normal anthelix.

The remaining part of the ear fold that constitutes the new anthelix is mainly kept unaffected by the clamp if the two legs of the clamp, prior to mounting around the cartilage fold, have a mutual first angle which is smaller than or equal to 90° and, after mounting around the cartilage fold, is mechanically forced in to a second angle which is smaller than or equal to the first angle. This particular U-shape or V-shape will cause two opposite points on the shaped anthelix of the excessively deformed ear to be affected by a deformation force giving the necessary compression, stretching and pulling of the cartilage for this cartilage to be lesioned to heal in normal anthelix form. The greater part of the fold tissue is not affected by the clamp as this part of the tissue is only surrounded by the clamp without contacting it.

BRIEF DESCRIPTION OF THE DRAWINGS

The invention will be explained in greater details below, describing only exemplary embodiments with reference to the drawing, in which FIG. 1a is a side elevational perspective view of a first embodiment of a clamp according to the invention, FIG. 1b is a front perspective view of the clamp in FIG. 1, FIG. 2 is a perspective view of a second embodiment of a clamp according to the invention.

DETAILED DESCRIPTION OF THE PREFERRED EMBODIMENTS

Figure 3:
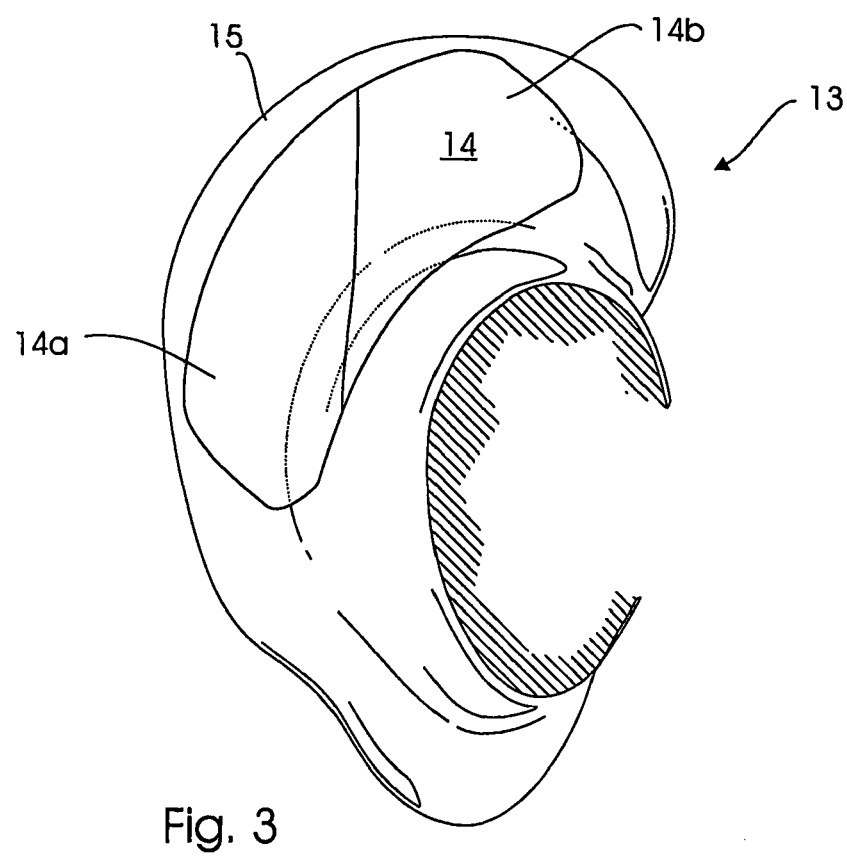
FIG. 3 is a perspective view of an ear viewed from the back with an attached fixture.

In a preferred embodiment the clamp has a longitudinal extent which mainly corresponds to the length of the anthelix of a normal ear to thereby exert an approximately uniform clamping force from opposite outer sides of the fold in its entire extent. Alternatively a number of smaller, correspondingly shaped clamps can be mounted side by side along the cartilage fold.

A preferred material for the clamp according to the present invention is metal, as metals are known to be able to maintain their shape after deformation. The legs of a metal clamp extending over a cartilage fold can advantageously be squeezed towards each other until opposite areas along the inner side of the two legs are contacting and squeezing on corresponding edge areas along the outer side of the cartilage fold. The angle between the legs is reduced by e.g. pressing on the outer side of the legs until the clamp has been deformed to the desired extent. The metal maintains the forced deformation, and the compressive and stretching forces on the intended areas of the fold are kept constant until the clamp is removed. Preferred metals are allergy tested silver and silver alloys and also titanium and titanium alloys having suitable deformation properties. Elastic materials having similar deformation properties can also be used within the scope of the invention.

If the clamp is used at night for example, the patient might unintentionally assume a position in which a sharp metal edge could damage the exterior ear by e.g. cutting into areas of this. In order to prevent this, the inside face of the clamp can be covered by a protective pad, for example a nonallergenic soft foam pad. Such a pad will furthermore prevent the blood supply from being cut off and skin irritation when the clamp is made to tighten and squeeze around the cartilage fold to the necessary extent. The pad can e.g. be glued to the inside face of the clamp and can advantageously extent at least a short distance, for example 2 mm beyond the edge of the clamp to shield this clamp.

For some patients, it would be especially expedient to let the free ends of the legs converge in an arc-shape towards each other so that the clamp projects the least possible from the ear in use. Advantageously this protective pad extends past the free end of the legs also in this case to make absolutely sure that the ends do not damage the ear when the clamp is pressed together around the ear fold.

The angle between the legs of the clamp is especially easy to adjust and maintain by means of a screw clamp affecting opposite points on the exterior face of the clamp legs. The screw clamp can e.g. be shaped as an ear ring with an adjusting screw, by which one of the clamp legs is forced towards the second clamp leg.

The clamp according to the present invention can be used alone but is preferably used in combination with the inventor's above-mentioned devices according to the International Patent Applications No. WO 00/09050 and WO 01/06967. If a combined use is preferred, a first initial stage of the artificial anthelix is made by means of an adhering fixture. Then the clamp according to the present invention is mounted in such a way that an excessively deformed anthelix is maintained. This treatment stage is performed and maintained typically over night, after which the clamp according to the invention is taken off during day time. The fixture keeps the anthelix in deformed position during the day, and the treatment is possibly supplemented during the day by using the device according to the International Patent Application No. WO 00/09050. This treatment cycle is repeated until a fully healed and permanent anthelix formation is established.

As no two ears necessarily require identical treatment, the above treatment regime is naturally only to be taken as an example.

The symmetrical clamp 1 in FIGS. 1a and 1b has two legs 2,3 with a mutual first angle α of 90° or less when the clamp 1 is not in use. The clamp 1 is made of a relatively thin metal plate, for example a silver sheet, which is bent into a V forming the two legs 2, 3 of the clamp. The thickness of the silver sheet material is typically between 0.2 and 2 mm. Between the legs 2,3, a protective pad 4 is attached, covering in the case shown the entire surface of the gap between the legs 2,3 and extending by a portion 7,8 past the free ends 5,6 of the legs. The portion 7,8 follows the shape of the ear and prevents the thin metal sheet from damaging the ear. Even if the pad 4 is shown here to cover the entire inside face of the clamp, the pad 4 can have any other thickness or form within the scope of the invention. For example the pad 4 can have slots or holes. It is preferred that the thickness of the pad 4 is between 1 and 4 mm, and that the pad is glued inside the V. An adhesive 9 for gluing the clamp 1 onto an anthelix covers the area of the inside face of the pad 4 that is to be glued onto the ear.

The clamp 1 has an arc-shaped upper end edge 10a, 10b facing upwards in use, and an arc-shaped lower end edge 11a,11b facing downwards in use. The legs 2,3 are longer at the upper end edge 10a,10b than at the lower end edge 11a, 11b. The free end edges 12a, 12b of the legs have a concave central part in the embodiment shown, so that the risk of the clamp 1 damaging concha and/or scarpha is the least possible.

The second and more simple embodiment in FIG. 2 of a clamp 1' according to the invention corresponds to the one in FIGS. 1a and 1b, and like parts are similarly referenced. The clamp 1' only differs by the legs 2',3' having straight free end edges 12a',12b'. This embodiment is especially easy and inexpensive to produce and would be suitable for the vast majority of patients. Alternatively, the two legs of the clamp can overall in a flattened state have a butterfly-like shape, but many other shapes are comprised within the scope of the invention.

Figure 4:
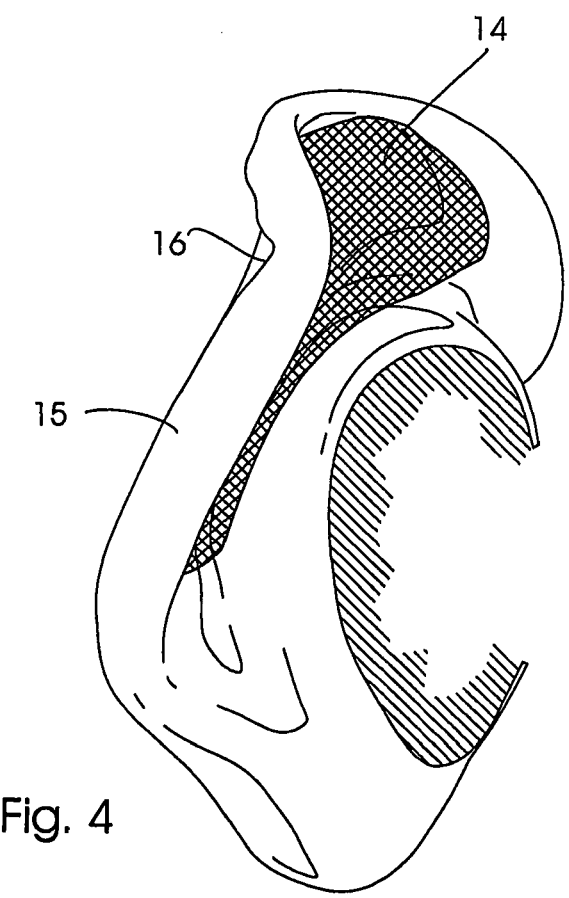
FIG. 4 is a perspective view of the ear in FIG. 3 with a partly artificial anthelix fold.
Figure 5:
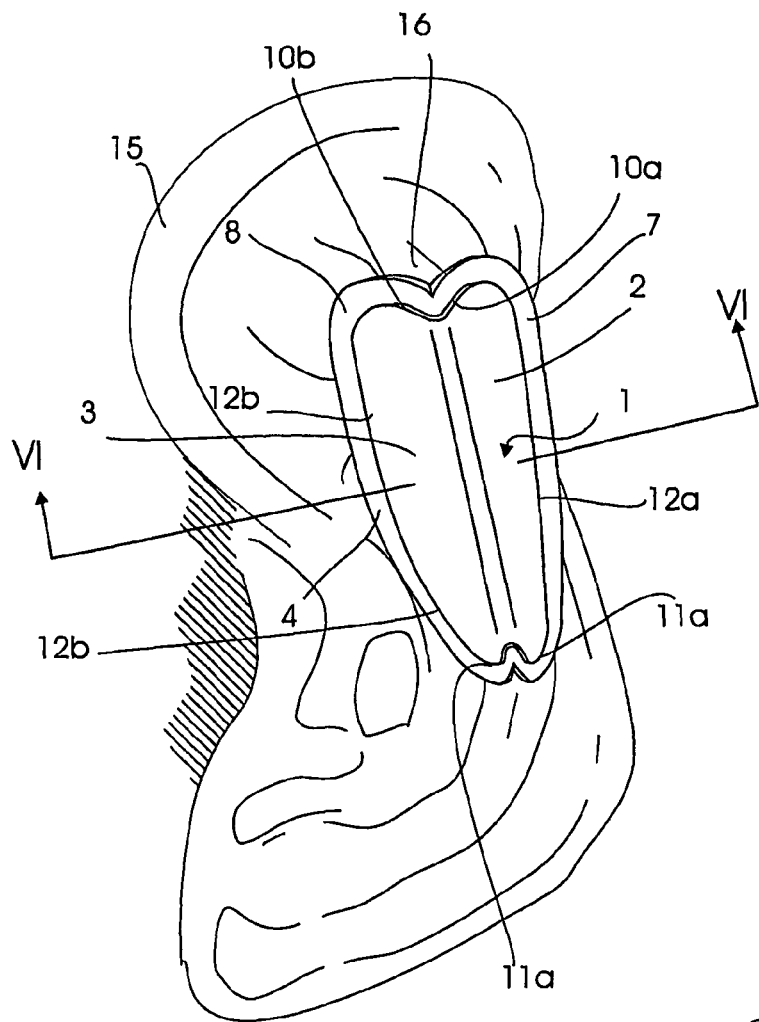
FIG. 5 is a perspective view of the ear in FIG. 4 viewed from the front with the clamp of FIG. 1 attached over the artificial anthelix fold.

In the following, the use of the clamp will be described in detail. In FIG. 3, a jug-ear 13 is seen from behind. The jug-ear 13 is shown separated from the head for the sake of clearness as the head otherwise would partly cover exactly the parts that are to be illustrated. On the back of the ear 13, a fixture 14 is attached, which is shown covered by a protective film 14a, 14b. In FIG. 4, the protective film has been removed and the back of the helix 15 of the ear 13 is shown partly folded backwards so that the fixture 14 is glued to itself along a folding line. The fixture 14 keeps the ear 13 in an excessively deformed shape to form an anthelix. The ear 13 is seen from the front in FIG. 5. The clamp 1 is glued onto the front of the artificially formed anthelix 16 which in addition is kept solidly stuck together by the fixture 14.

Figure 6:
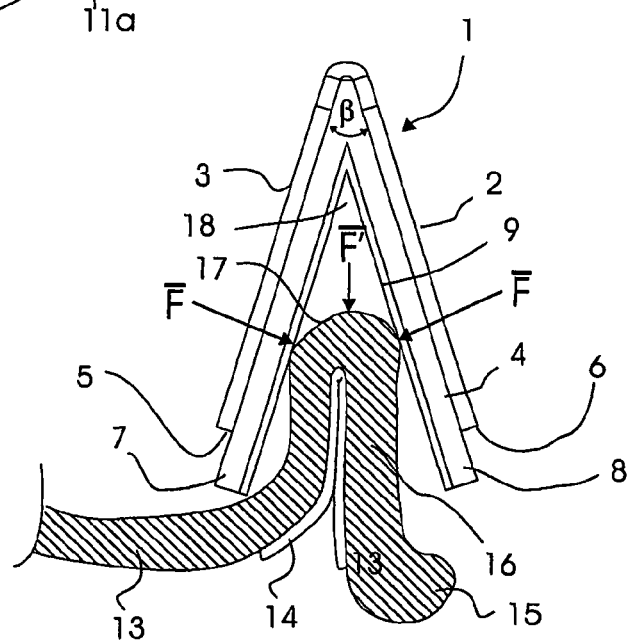
FIG. 6 is a sectional view taken along the line VI-VI of FIG. 5.

As seen best in FIG. 6, the clamp 1 extends over an anthelix 16. The second angle β, which is smaller than the first angle α, between the legs 2,3 has been forced on the clamp by an exterior force application causing a longitudinal local area on either side of the folded anthelix 16 to be affected by a force $\vec{F}$ perpendicular to the legs 2,3. The vertical component $\vec{F}'$ of the force $\vec{F}$ exerts a pull on the vertex 17 of the anthelix 16 which makes the cartilage fibers in this area to break. As seen in FIG. 6, the clamp 1 leaves an empty headspace 18 above the vertex 17. The part of the legs that is extending from the working point of the force $\vec{F}$ to the free ends 5,6 of the legs does not contact the ear. The very small contact area between the clamp and the ear means that patient is not bothered by the treatment.

Figure 7:
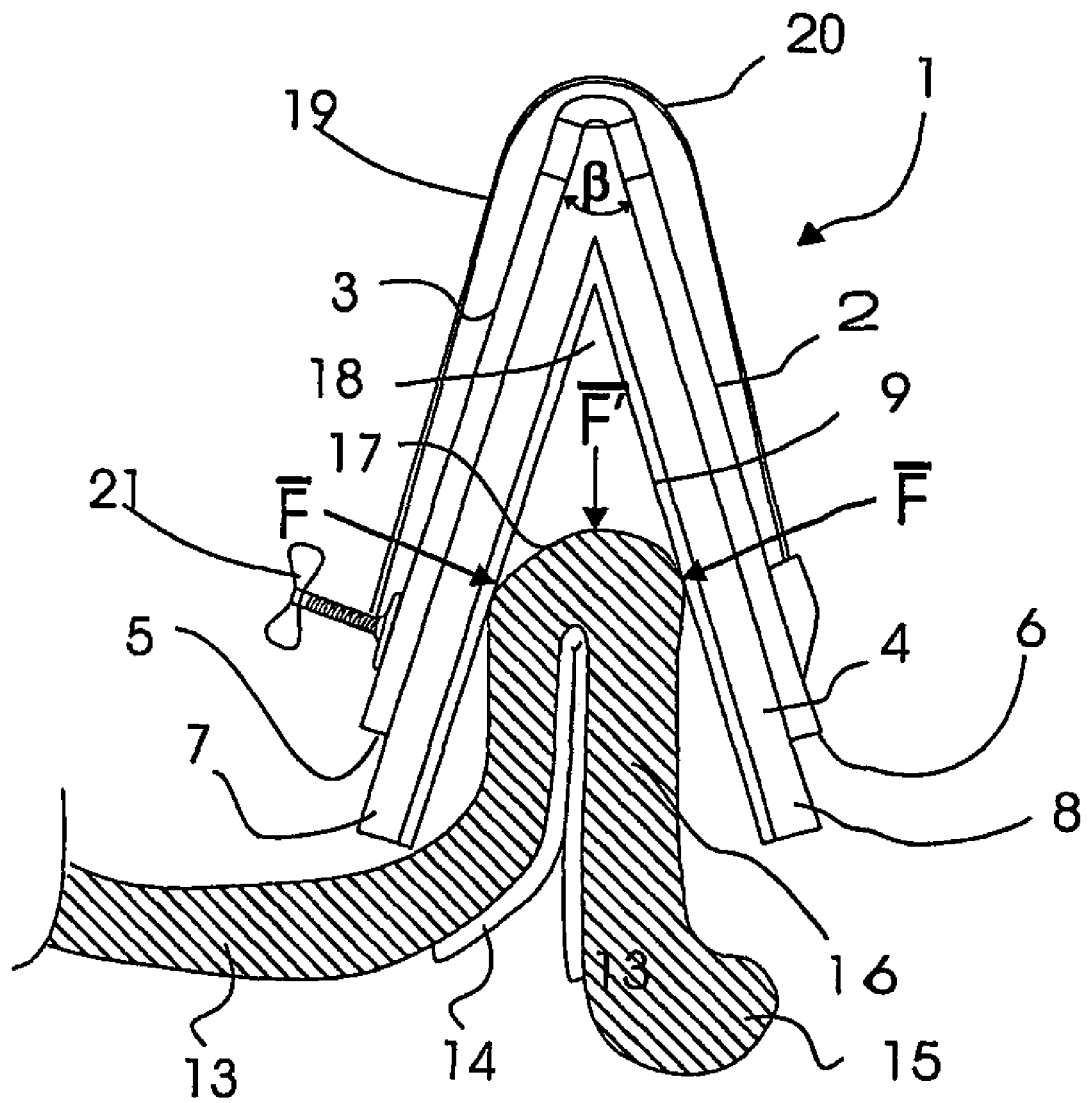
FIG. 7 is a sectional view of a third embodiment of a clamp according to the invention mounted around an artificially shaped anthelix fold.

FIG. 7 shows a modification of the clamp 1 of FIG. 6, which furthermore has a screw clamp 19 mounted on the outside of the clamp 1. The screw clamp has a bracket 20 firmly anchored on the leg 2 and a clamp screw 21 diametrically opposite, which is bearing on the second leg 3 with a foot. By means of the clamp screw 21 the force, by which the legs 2,3 press on anthelix 16, can be increased further, and the screw clamp 19 furthermore serves for increasing the adhesive grip of the clamp 1 on the ear 13.

The preferred material for the clamp 1,1' according to the invention is a material that can keep a permanent deformation, for example metals of silver, silver alloys, titanium or titanium alloys. Such materials can maintain a constant compressive force and clamping force in use on an exterior jug-ear which is to be treated for lacking anthelix.

The treatment with the clamp according to the present invention can permanently change the shape of the exterior ear so that the patient avoids surgery. Thus, the treatment can completely replace surgery.

What is claimed is:

1. A clamp in the form of a mainly V-shaped device for non-invasively affecting a cartilage fold on an exterior ear of a person by applying stretching and compressive forces, which clamp comprises first and second legs that are arranged in a V shape and are made of a material having properties sufficient to be given a permanent deformation to maintain a constant pressure on local, opposite areas of the cartilage fold of the exterior ear and to maintain the constant pressure and the stretching and compressive forces until the clamp is removed, wherein the first and second legs of the clamp prior to use have a mutual first angle α which is smaller than or equal to 90°, and wherein the clamp in use extends over the cartilage fold, with the first and second legs permanently deformed to assume a second angle β which is smaller than the first angle α, wherein the first and second legs have free ends that are arc-shaped and converge mutually towards each other.

2. The clamp according to claim 1, wherein the clamp has a longitudinal extent that mainly corresponds to the length of the anthelix of the exterior ear.

3. The clamp according to claim 1, wherein the clamp is made of metal.

4. The clamp according to claim 3, wherein the metal is silver, a silver alloy, titanium or a titanium alloy.

5. The clamp according to claim 1, wherein the first and second legs each have a generally linear free end.

6. The clamp according to claim 1, which further comprises a protective pad provided which is supported by the first and second legs.

7. The clamp according to claim 6, wherein the protective pad is at least partly covered by an adhesive which detachably adheres to human skin.

8. The clamp according to claim 6, wherein the first and second legs are made of a metal sheet having a thickness of between 0.2 and 2 mm and the protective pad is made of nonallergenic foam material and covers the entire surface of the legs and extends by a portion past the free ends of the legs.

9. The clamp according to claim 8, wherein the protective pad extends at least 2 mm beyond the free ends of the legs, has one surface that is glued to the legs and an opposing surface that is at least partly covered by an adhesive which detachably adheres to human skin.

10. The clamp according to claim 9, which further comprises a screw clamp for adjusting and exerting pressure on the legs for maintaining the given angle β therebetween.

11. The clamp according to claim 1, which further comprises a screw clamp for adjusting and maintaining a given angle β between the first and second legs.

12. A method of forming an anthelix on an exterior ear that lacks a natural anthelix, which method comprises:
    forming, on the exterior ear of a person in need thereof, an artificial anthelix in the form of a fold which is maintained in a folded position from the inner side of the fold by means of a double coated fixture,
    deforming the cartilage for a first time period in at least an area of the fold by the clamp according to claim 1,
    optionally, for a second time period, maintaining the shape of the deformed fold between a female mold and a male mold, and
    repeating the previous steps until a healed, cosmetically satisfying anthelix is established.

13. The method according to claim 12, wherein the clamp maintains the ear in an excessively deformed state, in which the clamping force is only exerted on a local area of the artificially constructed cartilage fold, while the vertex of the ear fold is stretched and pulled until a permanent lesion is formed, such that healing of the lesion with cartilaginous scar tissue assists in forming of the cartilage structure of a normal anthelix.

14. The method according to claim 13, wherein the remaining part of the ear fold that constitutes the new anthelix is mainly kept unaffected by the clamp by surrounding the greater part of the fold tissue by the clamp without contacting it.

15. The method according to claim 14 which further comprises attaching a fixture to the back of the ear to keep the ear in an excessively deformed shape to form the anthelix.

16. The clamp according to claim 1 having an arc-shaped upper end edge facing upwards in use, and an arc-shaped lower end edge facing downwards in use, wherein the legs are longer at the upper end edge than at the lower end edge.

17. The clamp according to claim 1 which further comprises a fixture attached to the back of the ear to keep the ear in an excessively deformed shape to form the anthelix.

* * * * *